(12) United States Patent
Krishnan et al.

(10) Patent No.: US 9,020,235 B2
(45) Date of Patent: Apr. 28, 2015

(54) SYSTEMS AND METHODS FOR VIEWING AND ANALYZING ANATOMICAL STRUCTURES

(75) Inventors: Arun Krishnan, Exton, PA (US); Marcos Salganicoff, Bala Cynwyd, PA (US); Xiang Sean Zhou, Exton, PA (US); Venkat Raghavan Ramamurthy, Malvern, PA (US); Luca Bogoni, Philadelphia, PA (US); Gerardo Hermosillo Valadez, West Chester, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 203 days.

(21) Appl. No.: 13/363,753

(22) Filed: Feb. 1, 2012

(65) Prior Publication Data

US 2012/0172700 A1  Jul. 5, 2012

Related U.S. Application Data

(63) Continuation-in-part of application No. 13/111,376, filed on May 19, 2011, now Pat. No. 8,625,869.

(60) Provisional application No. 61/347,064, filed on May 21, 2010, provisional application No. 61/438,753, filed on Feb. 2, 2011.

(51) Int. Cl.
*G06K 9/00* (2006.01)
*A61B 6/00* (2006.01)
(Continued)

(52) U.S. Cl.
CPC ............. *A61B 6/5217* (2013.01); *G06T 7/0012* (2013.01); *G06T 2207/10116* (2013.01);
(Continued)

(58) Field of Classification Search
USPC ......... 382/128, 131, 132; 128/922; 378/4, 21; 600/425, 426, 427
See application file for complete search history.

(56) References Cited

U.S. PATENT DOCUMENTS 5,582,189 A    12/1996  Pannozzo
5,970,499 A  * 10/1999  Smith et al. .......................... 1/1
(Continued)

FOREIGN PATENT DOCUMENTS

WO    2009145170 A1    12/2009

OTHER PUBLICATIONS

Hong Shen et al., "Localized Priors for the Precise Segmentation of Individual Vertebras from CT Volume Data", Sep. 6, 2008, Medical Image Computing and Computer-Assisted Intervention a MICCAI 2008 [Lecture Notes in Computer Science], Springer Berlin Heidelberg, Berlin, Heidelberg, pp. 367-375.

(Continued)

*Primary Examiner* — Shervin Nakhjavan
(74) *Attorney, Agent, or Firm* — Peter R. Withstandley

(57) ABSTRACT

Systems and methods for supporting a diagnostic workflow from a computer system are disclosed herein. In accordance with one implementation, a set of pre-identified anatomical landmarks associated with one or more structures of interest within one or more medical images are presented to a user. In response to a user input selecting at least one or more regions of interest including one or more of the pre-identified anatomical landmarks, the user is automatically navigated to the selected region of interest. In another implementation, a second user input selecting one or more measurement tools is received. An evaluation may be automatically determined based on one or more of the set of anatomical landmarks in response to the second user input.

31 Claims, 13 Drawing Sheets

(51) Int. Cl.
*A61B 6/03* (2006.01)
*G06F 19/00* (2011.01)
*G06T 7/00* (2006.01)
*A61B 5/055* (2006.01)
*A61B 5/00* (2006.01)

(52) U.S. Cl.
CPC .............. *A61B 5/055* (2013.01); *A61B 5/4504* (2013.01); *A61B 5/726* (2013.01); *A61B 5/7425* (2013.01); *A61B 5/7485* (2013.01); *A61B 6/032* (2013.01); *A61B 6/469* (2013.01); *A61B 6/505* (2013.01); *A61B 5/743* (2013.01); *G06F 19/321* (2013.01)

(56) References Cited

U.S. PATENT DOCUMENTS

| | | | |
|---|---|---|---|
| 6,501,826 B1 | 12/2002 | Kropfeld | |
| 6,674,883 B1* | 1/2004 | Wei et al. | 382/132 |
| 6,928,314 B1* | 8/2005 | Johnson et al. | 600/407 |
| 8,160,395 B2* | 4/2012 | Sirohey et al. | 382/294 |
| 8,160,676 B2* | 4/2012 | Gielen et al. | 600/427 |
| 2006/0285730 A1* | 12/2006 | Habets et al. | 382/128 |
| 2007/0003124 A1* | 1/2007 | Wood et al. | 382/131 |
| 2007/0274585 A1* | 11/2007 | Zhang et al. | 382/132 |
| 2008/0044074 A1* | 2/2008 | Jerebko et al. | 382/128 |
| 2008/0232661 A1* | 9/2008 | Habets et al. | 382/128 |
| 2008/0242953 A1* | 10/2008 | Dew et al. | 600/300 |
| 2009/0069665 A1* | 3/2009 | Valadez et al. | 600/410 |
| 2009/0129644 A1* | 5/2009 | Daw et al. | 382/128 |
| 2009/0161937 A1* | 6/2009 | Peng et al. | 382/131 |
| 2009/0209866 A1* | 8/2009 | Abovitz et al. | 600/476 |
| 2009/0316975 A1* | 12/2009 | Kunz et al. | 382/131 |
| 2010/0082365 A1 | 4/2010 | Noordvyk | |
| 2010/0104152 A1* | 4/2010 | Abdelnour et al. | 382/128 |
| 2010/0303314 A1* | 12/2010 | Chen et al. | 382/128 |
| 2011/0110576 A1* | 5/2011 | Kreeger et al. | 382/132 |
| 2011/0249882 A1* | 10/2011 | Bornfleth | 382/132 |
| 2011/0289441 A1* | 11/2011 | Venon et al. | 715/771 |
| 2013/0279775 A1* | 10/2013 | Batman et al. | 382/128 |

OTHER PUBLICATIONS

International Search Report of Application No. PCT/US2011/037279 dated Aug. 17, 2011.

* cited by examiner

SYSTEMS AND METHODS FOR VIEWING AND ANALYZING ANATOMICAL STRUCTURES

CROSS-REFERENCE TO RELATED APPLICATIONS

This application claims the benefit of U.S. provisional application No. 60/438,753 filed Feb. 2, 2011, the entire contents of which are incorporated herein by reference.

This application is also a continuation-in-part of co-pending U.S. patent application Ser. No. 13/111,376 filed May 19, 2011 entitled "Visualization of Medical Image Data with Localized Enhancement," which claims the benefit of U.S. provisional application No. 61/347,064 filed May 21, 2010, all of which are hereby fully incorporated herein by reference.

TECHNICAL FIELD

The present disclosure relates generally to diagnostic imaging and, more specifically, to improved systems and methods for viewing and automatically analyzing anatomical structures in medical images.

BACKGROUND

The field of medical imaging has seen significant advances since the time X-ray images were first used to determine anatomical abnormalities. Medical imaging hardware has progressed in the form of newer machines such as medical resonance imaging (MRI) scanners, computed axial tomography (CAT) scanners, etc. Due to the large amount of image data generated by such modern medical scanners, there has been and remains a need for developing image processing techniques that can automate some or all of the processes to determine the presence of anatomical abnormalities in scanned medical images.

Recognition and processing of specific meaningful structures within a medical image may be referred to as automated advanced post-processing, which is a type of post-processing for medical imaging applications. One particularly useful image processing technique involves the imaging of the spinal column. A precise vertebra segmentation and identification method is in high demand due to its importance to, and impact on, many orthopedic, neurological, and ontological applications. For example, during the interpretation of spinal images, the radiologist often faces the tedious task of having to determine the level of spine and report the location of findings in terms of the cervical, thoracic and lumbar vertebrae or disk. In order to determine which vertebra is affected, the radiologist typically has to scroll and switch between sagittal and axial images many times. Without the aid of automated systems, such process is often very time consuming and error-prone.

Unfortunately, the task of segmenting and labeling vertebrae, even using automated post-processing techniques that are well-developed for other anatomical structures, often proves to be inaccurate and therefore inadequate. The difficulty lies in the inherent complexity of vertebrae. The variation within the same class of vertebra as well as the variation in neighboring structures makes vertebral modeling and imaging extremely difficult. Labeling becomes even more complicated in atypical cases where the vertebrae (or other spinal structures) have unusual characteristics (e.g., number, width, shape, size, etc.). In addition, imperfect image acquisition processes may result in noisy or incomplete scans that compound the difficulties of ascertaining the total number and positions of the vertebrae. Therefore, vertebrae often have to be manually labeled and corrected by the radiologist to ensure accuracy. This verification process, however, is also extremely time-consuming and error-prone, typically involving repeated scrolling of multiple images to check rib connections (e.g., lumbarization, sacralization, 11 or 13 T-spine, etc.) and labels of the vertebrae.

Accordingly, there is a need for improved systems and methods to facilitate efficient evaluation, labeling, and analysis of the spinal column and other anatomical structures.

SUMMARY

The present disclosure relates to a framework for supporting a diagnostic workflow from a computer system. In accordance with one implementation, a set of pre-identified anatomical landmarks associated with one or more structures of interest within one or more medical images are presented to a user. In response to a user input selecting at least one or more regions of interest including one or more of the pre-identified anatomical landmarks, the user is automatically navigated to the selected region of interest. In another implementation, a second user input selecting one or more measurement tools is received. An evaluation may be automatically determined based on one or more of the set of anatomical landmarks in response to the second user input.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
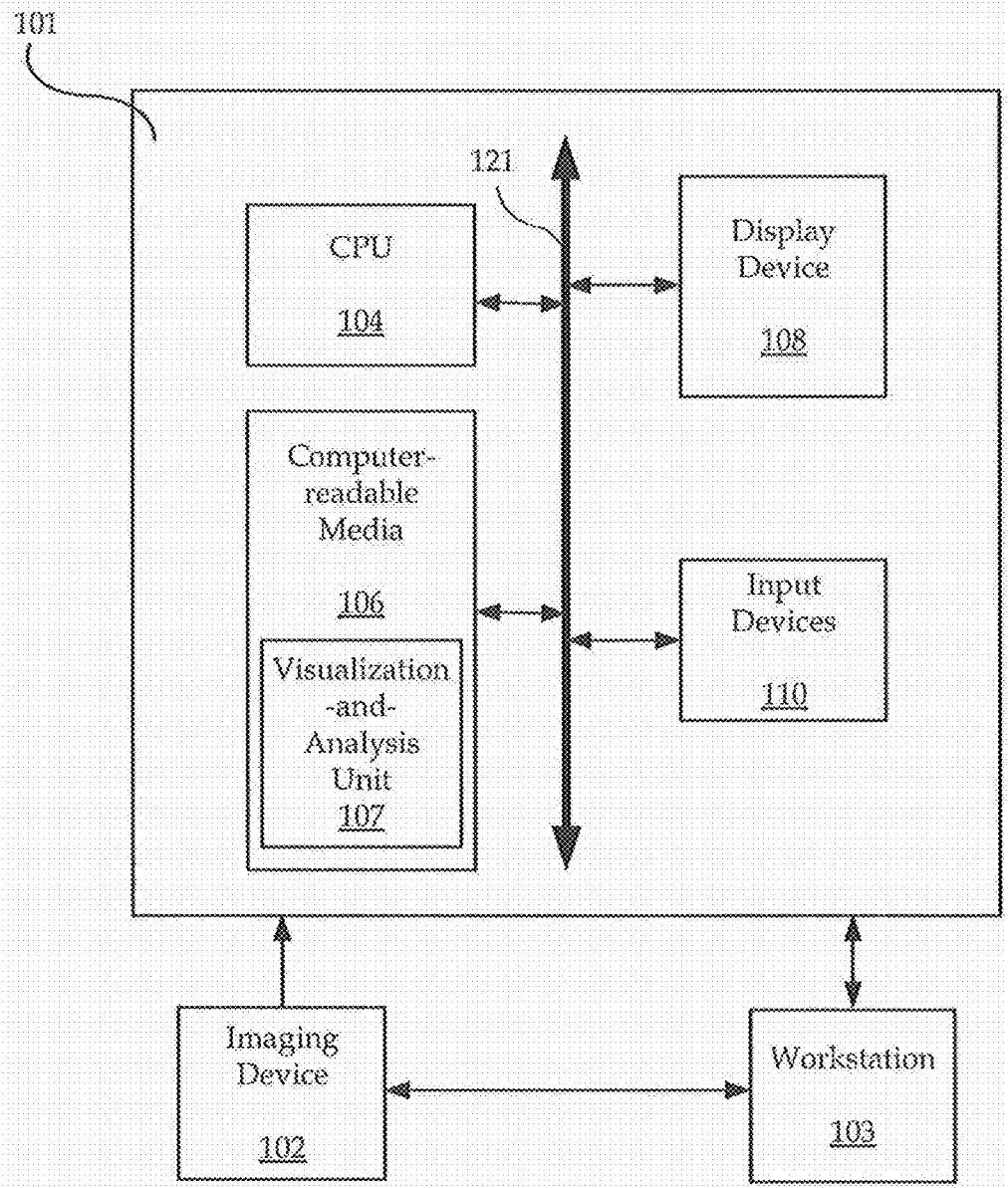
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulate and transform data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2D images and voxels for 3D images). The image may be, for example, a medical image of a subject collected by computer tomography (CT), magnetic resonance (MR) imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

In the following description, for purposes of explanation, specific numbers, materials and configurations are set forth in order to provide a thorough understanding of the present frameworks and methods and in order to meet statutory written description, enablement, and best-mode requirements. However, it will be apparent to one skilled in the art that the present frameworks and methods may be practiced without the specific exemplary details. In other instances, well-known features are omitted or simplified to clarify the description of the exemplary implementations of present frameworks and methods, and to thereby better explain the present frameworks and methods. Furthermore, for ease of understanding, certain method steps are delineated as separate steps; however, these separately delineated steps should not be construed as necessarily order dependent in their performance.

The present technology relates to automated or semi-automated visualization and analysis of digital or digitized medical images. In accordance with one implementation, a framework for supporting a diagnostic workflow from a computer system is provided. A graphical user interface may be constructed to interact with and display the output from the present framework. The present framework may provide for synchronized navigation between different images (or views) of a structure of interest, such as images acquired across multiple different modalities, acquisition protocol or time points. Tools may also be provided for generating optimized views of the structure or region of interest, automatically detecting and labeling anatomical landmarks, and/or performing quantitative evaluation based on the pre-identified anatomical landmarks. By facilitating many tasks (e.g., spine labeling, navigation, quantitative measurements, reporting, etc.) that are often encountered during a diagnostic workflow, the present framework advantageously enhances the speed, reliability and ease of analyzing medical images. These exemplary advantages and features will be described in more detail in the following description.

The present framework may be applied to musculoskeletal (MSK) analysis of the entire spine or portion thereof. However, it should be understood that while a particular application directed to viewing and analyzing MSK structures may be shown, the technology is not limited to the specific embodiments illustrated. The present technology has application to, for example, other types of anatomical structures (e.g., aorta, smaller branches near the aorta, blood vessels, vascular system, airways, brain, colon, etc.) as well as abnormalities or diseases associated with such anatomical structures. In addition, the present framework can be applied to image data acquired by one or more different imaging modalities, including but not limited to, magnetic resonance (MR) imaging, computed tomography (CT), helical CT, x-ray, positron emission tomography (PET), PET-CT, fluoroscopic, ultrasound, single-photon emission computed tomography (SPECT), SPECT-CT, MR-PET, etc.

FIG. 1 is a block diagram illustrating an exemplary system 100. The system 100 includes a computer system 101 for implementing the framework as described herein. Computer system 101 may be a desktop personal computer, a portable laptop computer, another portable device, a mini-computer, a mainframe computer, a server, a storage system, a dedicated digital appliance, a communication device, or another device having a storage sub-system configured to store a collection of digital data items. In some implementations, computer system 101 operates as a standalone device. In other implementations, computer system 101 may be connected (e.g., using a network) to other machines, such as imaging device 102 and workstation 103. In a networked deployment, computer system 101 may operate in the capacity of a server (e.g., thin-client server, such as Syngo®.via by Siemens Healthcare), a client user machine in server-client user network environment, or as a peer machine in a peer-to-peer (or distributed) network environment.

In one implementation, computer system 101 comprises a processor or central processing unit (CPU) 104 coupled to one or more non-transitory computer-readable media 106 (e.g., computer storage or memory), display device 108 (e.g., monitor) and various input devices 110 (e.g., mouse or keyboard) via an input-output interface 121. Computer system 101 may further include support circuits such as a cache, power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the micro-instruction code or as part of an application program or software product, or a combination thereof, which is executed via the operating system. In one implementation, the techniques described herein are implemented as computer-readable program code tangibly embodied in non-transitory computer-readable media 106. In particular, the present techniques may be implemented by visualization-and-analysis unit 107. Non-transitory computer-readable media 106 may include random access memory (RAM), read only memory (ROM), magnetic floppy disk, flash memory, and other types of memories, or a combination thereof. The computer-readable program code is executed by CPU 104 to process images (e.g., MR or CT images) acquired by, for example, imaging device 102 (e.g., MR or CT scanner). As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 106 may be used for storing visualization instructions, knowledge base, individual patient data, database of previously treated patients (e.g., training data), and so forth. The patient records, including associated image data, may be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The imaging device 102 may be a radiology scanner, such as a magnetic resonance (MR) scanner or a CT scanner, for acquiring image data. The workstation 103 may include a computer and appropriate peripherals, such as a keyboard and display device, and can be operated in conjunction with the entire system 100. For example, the workstation 103 may communicate with the imaging device 102 so that the image data collected by the imaging device 102 can be rendered at the workstation 103 and viewed on a display device. The workstation 103 may communicate directly with the computer system 101 to display processed image data and/or output image processing results. The workstation 103 may include a graphical user interface to receive user input via an input device (e.g., keyboard, mouse, touch screen voice or video recognition interface, etc.) to manipulate visualization and/or evaluation of the image data. For example, the user may view the presented image data, and specify one or more view adjustments or preferences, such as zooming, panning, rotating, changing contrast, changing color, changing view angle, changing view depth, changing rendering or reconstruction technique, navigate to a particular region of interest by specifying a "goto" location, and so forth.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

Figure 2:
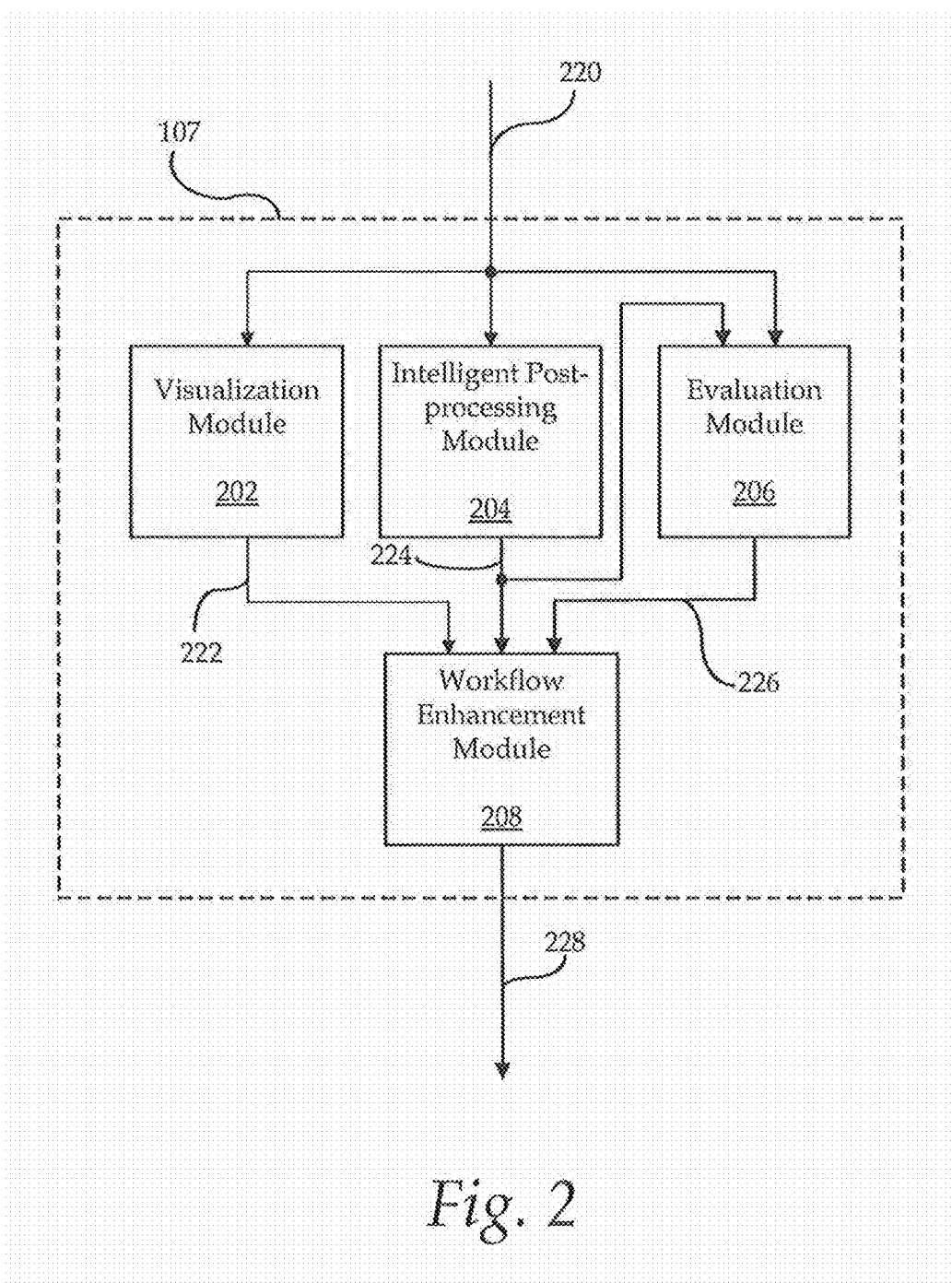
FIG. 2 shows an exemplary visualization-and-analysis unit.

FIG. 2 shows an exemplary visualization-and-analysis unit 107. In accordance with one implementation, the visualization-and-analysis unit 107 comprises four exemplary components—a visualization module 202, an intelligent post-processing module 204, an evaluation module 206 and a workflow enhancement module 208. It should be understood that additional, different, or fewer components may be provided. For examples, these exemplary components may be combined or separated into different modules, or additional components may be included.

In one implementation, the visualization module 202 receives image data 220 of a structure of interest and creates (or reconstructs) visual representations 222 for presentation to the user. Additionally, the visualization module 202 may also receive input from the user specifying viewing parameters or preferences. The structure of interest may include, for example, MSK structures (e.g., vertebrae, joints, muscles, cartilage, ligaments, other connective tissues, etc.), other anatomical structures (e.g., vascular structures, brain, etc.) and/or their associated abnormalities (or diseases). The visual representations 222 may represent one or more planes or manifolds of view (e.g., axial, sagittal, coronal, etc.), and be presented as one or more two-dimensional or three-dimensional images to a user using various rendering techniques (e.g., volume rendering or virtual reality rendering).

In addition, the visualization module 202 may create composite images with localized enhancement using techniques described in, for example, U.S. patent application Ser. No. 13/111,376 filed May 19, 2011, which is herein incorporated by reference in its entirety. Accordingly, the visual representations 222 may include a reconstructed maximum or minimum intensity projection image, a multi-planar reconstruction (MPR) image, a curved MPR image, a summation-based, an average-based or a filtering-based projection image, or a combination thereof. The visualization module 202 may further perform anatomical landmark-based image linking (or registration), as will be described in more details in the following sections.

In one implementation, the intelligent post-processing module 204 automatically or semi-automatically identifies (or detects) anatomical landmarks, abnormalities and/or diseases in the image data 220. In one implementation, the intelligent post-processing module 204 locates and labels anatomical landmarks 224, which are elements of the image data that have anatomical relevance (e.g., extremities of a vertebra). The anatomical landmarks 224 may be obtained cross-modally or cross-sequentially over time. These anatomical landmarks 224 may be used to obtain measurements that are not easily or practically obtainable in a single view. Additionally, or alternatively, the intelligent post-processing module 204 may also automatically detect abnormalities or diseases in the image data 220 to generate findings 224.

In one implementation, the evaluation module 206 generates measurements and/or other evaluation results 226 based on the detected anatomical landmarks (or CAD findings as applicable) 224 and/or image data 220. For example, the evaluation module 206 may automatically or semi-automatically perform MSK-related measurements, such as bone density, spine curvature, vertebral body height, inter-vertebrae distance, disk herniation, spinal canal stenosis, thecal sac diameter, listhesis (or slip of vertebra backward/forward), stenosis of foramina (or minimum diameter), conus of cord, sacral obliquity, pelvic obliquity, pelvic inclination, scoliosis measurements (e.g., Cobb angles), or the like. Other types of measurements or evaluation may also be determined. These features will be described in more details in the following sections.

The visualization-and-analysis unit 107 may further include a workflow enhancement module 208. In one implementation, the workflow enhancement module 208 combines the output (222, 224, 226) from the visualization module 202, intelligent post-processing module 204 and/or evaluation module 206, and generates a graphical user interface 228 for supporting a diagnostic workflow. Exemplary graphical user interfaces 228 will be further described in the following sections.

Figure 3:
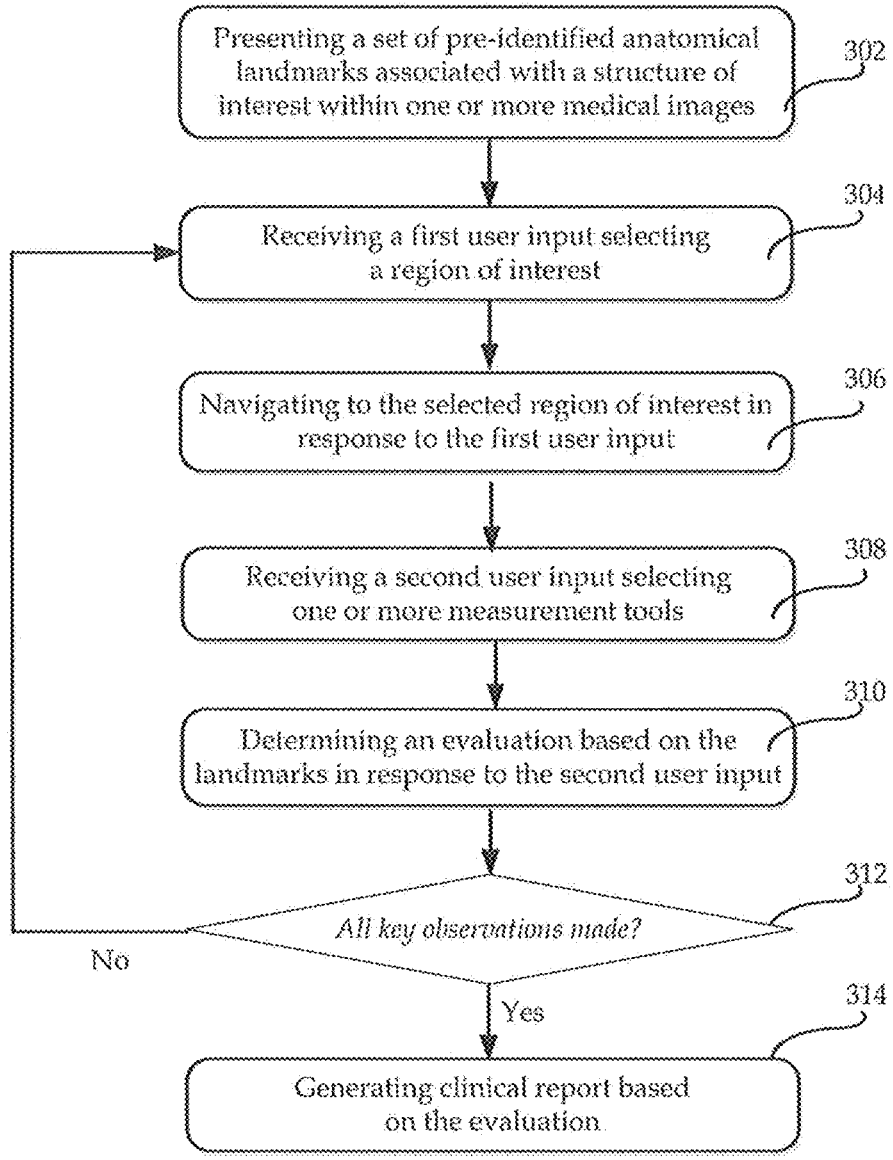
FIG. 3 shows an exemplary method for supporting a diagnostic workflow.

FIG. 3 shows an exemplary method 300 for supporting a diagnostic workflow from a computer system. The steps of the method 300 may be performed in the order shown or a different order. Additional, different, or fewer steps may be provided. Further, the method 300 may be implemented with the system 100 of FIG. 1, the visualization-and-analysis unit 107 of FIG. 2, a different system, or a combination thereof. The same or different systems can perform labeling and visualization of the structure of interest. For example, one computer system may be used for automatically segmenting and labeling the anatomical landmarks, and a different computer system may be used for creating (or reconstructing) the visual representations.

As shown in FIG. 3, at 302, a set of pre-identified anatomical landmarks associated with one or more structures of interest within one or more medical images is presented. The structures of interest may be any anatomical structures or portion thereof that have been identified for further study or examination, such as a musculoskeletal (MSK) structure (e.g., spine, vertebrae, joints, muscles, cartilage, ligaments) or any other anatomical structure (e.g., aorta, brain, colon, etc.). The set of anatomical landmarks may represent midpoints, extremities, or local regions of the structures of interest that are of anatomical relevance.

In one implementation, the medical images are extracted from a volumetric image data set. The medical images may include slice images that are obtained in the area of the structure of interest (e.g., spinal column, vertebrae, etc.) on the basis of previously determined tomographic data records. The orientation and position of individual structures of interest may be automatically identified, and appropriate slices defined, in the tomographic data records. Exemplary techniques for automatically obtaining such slice images are described in, for example, U.S. Pat. No. 7,835,497 filed Feb. 15, 2008, which is herein incorporated by reference in its entirety.

The volumetric image data set may be stored in Digital Imaging and Communications in Medicine (DICOM) format. Any other digital file format may also be used. The medical images may be received from, for example, a storage device, a database system or an archiving system, such as a picture archiving and communication (PACS) system. In addition, the medical images may be acquired by, for example, the imaging device 102 using techniques such as magnetic resonance (MR) imaging, computed tomography (CT), helical CT, x-ray, positron emission tomography (PET), PET-CT, fluoroscopic, ultrasound, single-photon emission computed tomography (SPECT), SPECT-CT, MR-PET, etc. Further, the medical images may be two-dimensional, three-dimensional, or four-dimensional.

Figure 4:
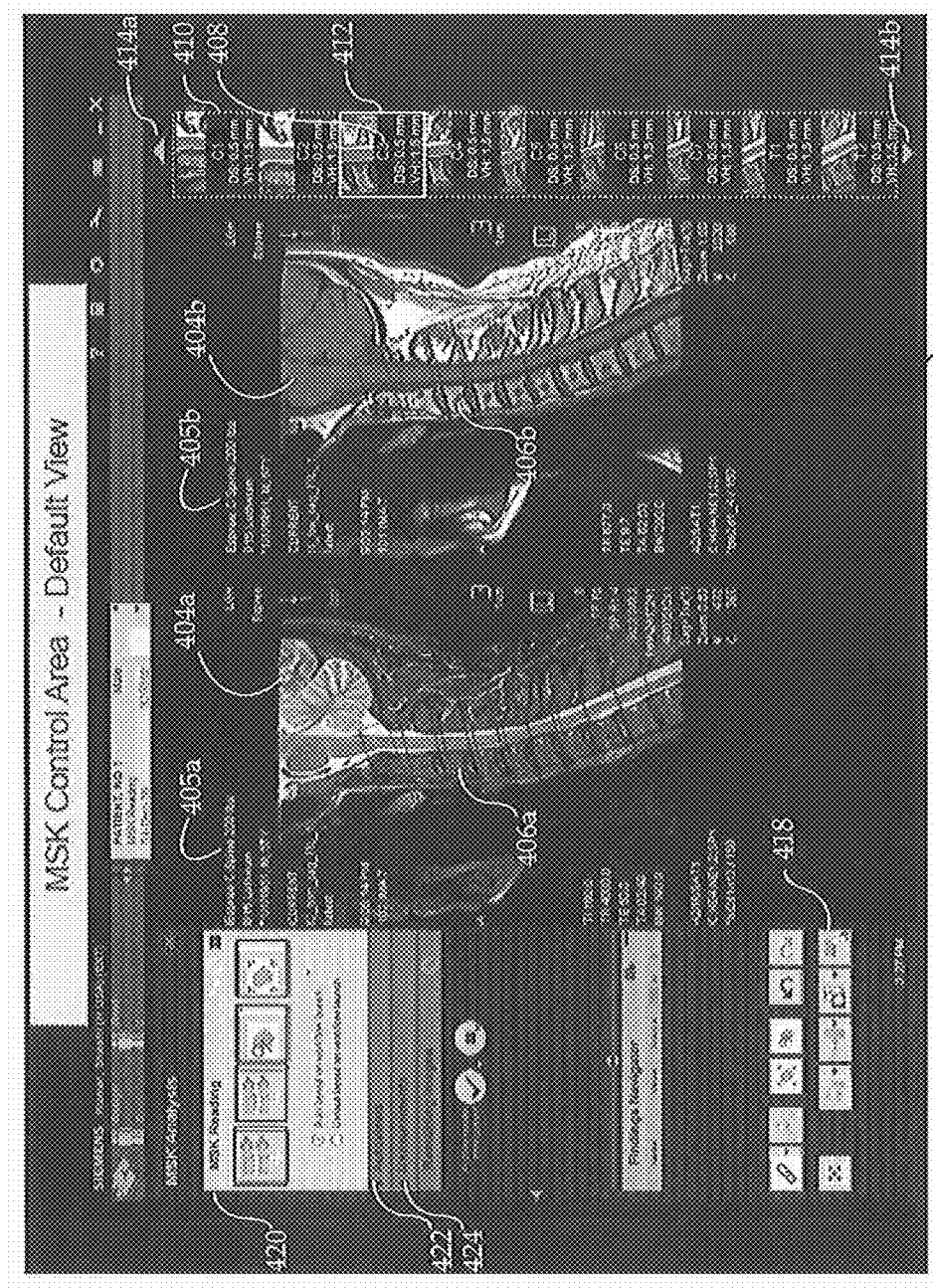
FIG. 4 shows an exemplary graphical user interface.

In one implementation, the medical images are created (or reconstructed) by the visualization module 202. The medical images may be presented to the user via a graphical user interface 228 generated by the workflow enhancement module 208. FIG. 4 shows a graphical user interface 228. Although the exemplary graphical user interface 228 is designed for supporting the diagnostic workflow for MSK analysis, it should be understood that such embodiment is meant to be illustrative and not limited to the specific case of MSK analysis. The core innovations described herein have applications to many other different applications.

Referring to FIG. 4, a default view of a graphical user interface 228 is shown. As shown, the graphical user interface 228 may display MRI acquisitions 404a-b of a vertebral column of a patient using different acquisition protocols. The chest radiographs may be obtained as either postero-anterior (PA) or antero-posterior (AP) images. It should be understood that while two images are shown, one or more than two images may also be displayed. The medical images 404a-b may have been acquired at different points in time. In addition, the medical images may be collected from multiple studies across different modalities or by a single modality at different times. The medical images may also be acquired by the same modality using different acquisition protocols (e.g. reconstruction parameters or MRI pulse sequences).

In one implementation, optimal views of the medical images 404a-b are created (or reconstructed). The images may be rotated, translated or scaled for proper viewing. In addition, the medical images 404a-b may be created as maximum or minimum intensity projection images, multi-planar reconstruction (MPR) images, curved MPR images, summation-based, average-based or filtering-based projection images, or a combination thereof. In another implementation, the medical images 404a-b comprise a curved planar reformat (CPR) view of the structure of interest. To create the CPR image, sagittal or coronal reformat curvilinear coordinates of the images may be spatially aligned with, for example, the coordinates of the principal bony structures of the spine (e.g., spinal canal, vertebrae, spinous processes, etc.).

The optimal views may further be created by normalizing (or correcting) medical images 404a-b to improve visualization. In the case of MR images, for instance, normalization may be performed based on the MR signal to soft-tissue intensity. In one implementation, the medical images 404a-b are normalized by using the typical minimum and maximum signal intensity values of known soft tissue areas to rescale the signal intensity values of the rest of the image from minimum to maximum values. The medical images 404a-b may also be scaled or coded. This allows the MR signal of marrow (or medullar) areas (e.g., bone) to be compared with the signal intensity of soft tissue areas (e.g., muscle). Other types of normalization may also be performed.

As discussed previously, the medical images 405a-b may include anatomical landmarks 406a-b that have been previously detected (or identified). The anatomical landmarks 406a-b may be detected automatically or semi-automatically by, for example, the intelligent post-processing module 204. Alternatively, the user may manually identify the anatomical landmarks 406a-b via the graphical user interface 228. In one implementation, an image processing technique is performed to automatically identify the anatomical landmarks. Various types of image processing techniques may be applied to detect the anatomical landmarks, including thresholding, region-growing, segmentation or edge detection algorithms. In one implementation, the image processing technique is a machine learning-based algorithm that trains a discriminative classifier based on a set of training samples. An exemplary machine learning-based algorithm is described in U.S. Pat. No. 7,876,938 filed Oct. 3, 2006, the disclosure of which is herein incorporated by reference in its entirety.

Alternatively, or in combination thereof, a user interface may be provided to accept user input identifying one or more points located inside a component (e.g., vertebra) of the structure of interest (e.g., vertebral column). The user-provided points may be used to, for example, seed a region-growing algorithm, adaptive thresholding technique or any other technique that can segment and identify regions around the user-provided points. Additionally, the orientation of the anatomical landmarks may also be automatically or semi-automatically determined. For example, intervertebral disc orientation may be determined by estimating an orientation field or a centerline from segmented vertebrae regions. It should be understood that other techniques may also be employed.

Figure 5A:
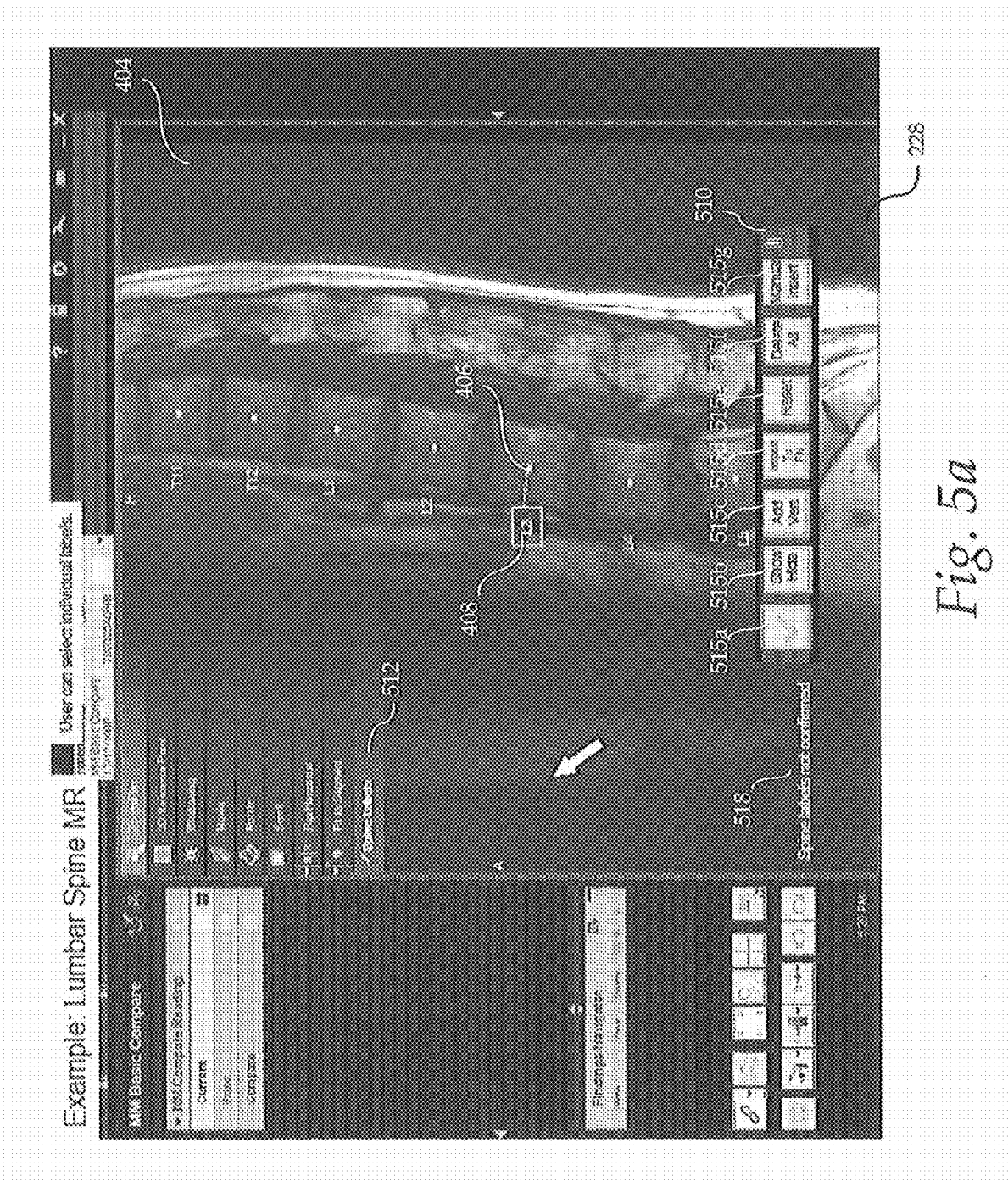
FIG. 5a shows an exemplary graphical user interface with a label editing toolbar.

FIG. 5a shows an exemplary graphical user interface 228 with a label editing toolbar 510 in accordance with one implementation. An MR image 404 with pre-identified anatomical landmarks 406 along the lumbar spinal column is displayed. Each anatomical landmark 406 may be presented by displaying an indicator (e.g., a dot, cross, line, box, text label, etc.) located at, around or near the anatomical landmarks. Text labels 408 (e.g., T11, T12, L1, L2, L3, etc.) may be displayed with optional lead lines ending at or near the anatomical landmarks 406.

In one implementation, the labels 408 are automatically assigned to the landmarks 406. The labels may be assigned in accordance with a standard naming convention. For example, in the context of labeling the individual vertebrae of a human spine, the standard C1-C7, T1-T12, L1-L5 and S1-S5 naming convention may be followed to label the 7 cervical, 12 thoracic, 5 lumbar and 5 sacral vertebrae respectively. Other types of naming conventions may also be applied. The labeling direction may be, for example, in the head-to-feet direction starting at the first thoracic vertebra T1.

Optionally, instead of performing the automatic label assignment algorithm repeatedly on all series of images, detected landmarks in one or more label scout images (or localizers) or a "key series" may be automatically labeled. Such automatically assigned labels may then be propagated (or shared) and displayed in other images of all series that share a common frame of reference with the scout images or "key series".

The user may choose to turn the automatic labeling on or off by selecting the menu option 512. In addition, the user may also move the label, select individual labels for editing or change the font size or type of the label text. The label editing toolbar 510 enables the user to configure the automatic labeling. For example, the user may validate or confirm the spine labels by selecting toolbar button 515a. A text warning 518 may be displayed when the spine labels are not confirmed. Once confirmed, the text warning 518 may automatically disappear. The user may also choose to show or hide the spine labels and/or indicators with a single click of button 515b. In addition, the user may insert one or more additional vertebra landmarks or labels, import to the findings navigator, revert to original vertebra labels or delete one or more vertebra landmarks or labels, by selecting respective toolbar button 515c, 515d, 515e, 515f or 515g. A confirmation pop-up window may be displayed if the user chooses to delete all the landmarks.

Figure 5B:
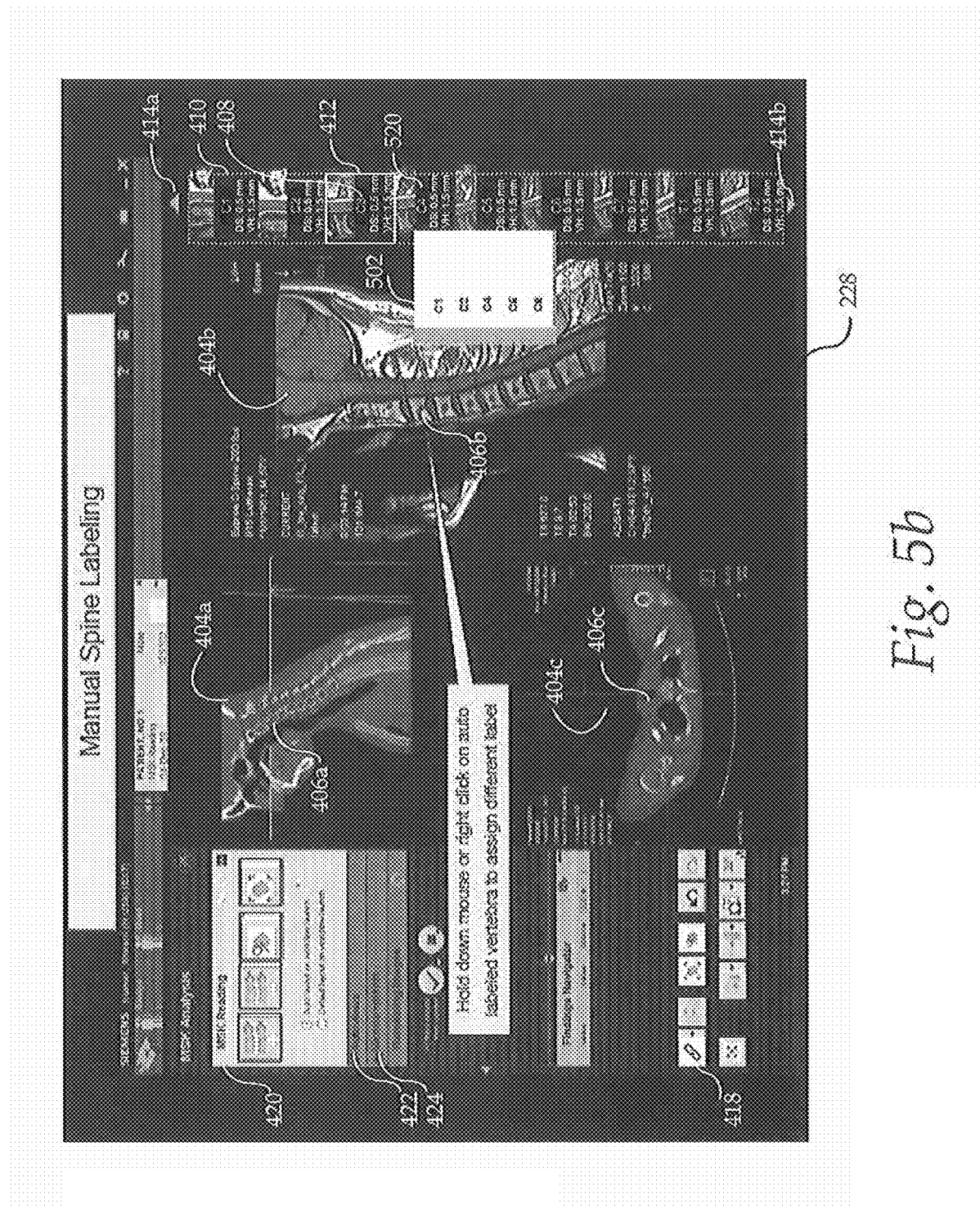
FIG. 5b shows an exemplary graphical user interface that allows automatically assigned labels to be manually changed.

FIG. 5b shows another exemplary graphical user interface 228 that enables the user to manually edit or modify the automatically assigned labels. As shown, landmark points 406a-c are detected along the vertebral column. The text labels 408 (e.g., C1, C2, C3, etc.) may be automatically assigned and displayed in a navigation window 410 of sub-images 412 representing local regions of interest. Each sub-image may contain at least one pre-identified anatomical landmark and its associated label, as will be described in more details in the following sections.

To manually re-assign a different label, the user may select the automatically detected vertebra in one of the images 404a-c by means of, for example, holding down the mouse key or right clicking on the vertebra. Other means of interaction, such as via a keyboard, a touch screen, a voice or video recognition device, may also be used to receive the user selection. Upon receiving the user selection, a drop-down menu 502 offering a list of pre-determined labels may be presented near the selected vertebra to enable the user to select a suitable label. In one implementation, the drop down menu 502 includes a cascaded hierarchical drop down menu for presenting different levels of a hierarchy of labels. The hierarchy of labels may be associated with different levels of abstraction of the structure of interest. For example, a first level of labels naming different vertebral segments (e.g., C, T, L, etc.) may be displayed. In response to a user selecting one of these vertebral segments (e.g., T), a second level of labels naming particular vertebrae (e.g., T1, T2, . . . , T12, etc.) of the selected segment may be displayed. The user may then select one of these second level labels. Alternatively, a text box may be presented to allow the user to type a name for the label as desired. The label 408 in the navigation window 410 may then be updated with the user-initiated changes.

The other neighboring labels 520 may also be automatically updated in response to the changes made to label 408. In one implementation, the neighboring labels 520 are automatically updated in accordance with the sort order defined by the naming convention used. For example, if a vertebra is relabeled with a new name (e.g., T3), other labels above it (e.g., C1-C2, T1, T2) or below it (e.g., T4-T12, L1-L15, S1-S5)

may be automatically updated to be in consistent with the sort order defined by the standard naming convention.

Figure 6:
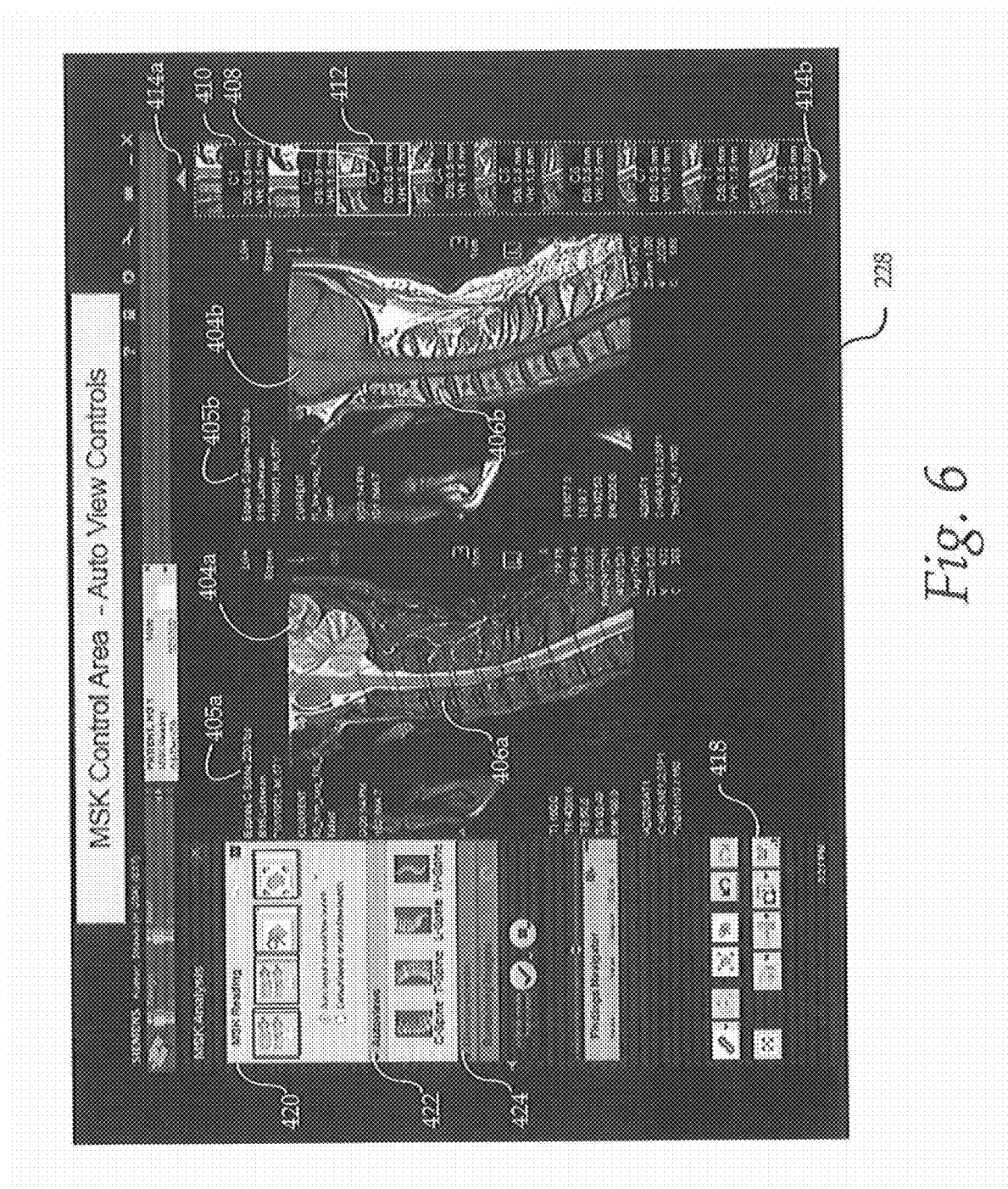
FIG. 6 shows an exemplary graphical user interface with an "Autoviews" menu.

Referring back to FIG. 3, at 304, a first user input selecting a region of interest is received. In one implementation, the first user input is received via an "Autoviews" menu. FIG. 6 shows an exemplary graphical user interface 228 with an exemplary "Autoviews" menu 422. The "Autoviews" menu 422 enables the user to select a pre-defined anatomical region of interest for viewing. In one implementation, the pre-defined region of interest corresponds to a structure of interest or a portion thereof. In the case of a vertebral column, for example, the pre-defined region of interest may correspond to a vertebral segment (e.g., C-spine, T-spine, L-spine or W-spine regions). Other types of regions of interest may also be pre-defined. For instance, in the case of a brain, the region of interest may correspond to the cerebral cortex, brain stem or cerebellum. As for the pulmonary system, the region of interest may correspond to the pulmonary artery, pulmonary vein, the right atrium, the left atrium, the venae cavae, aorta, right ventricle or left ventricle.

When the user selects the "Autoviews" menu 422, it is expanded to display a drop-down box with various graphical representations and labels of the pre-defined regions of interest (e.g., C-spine, T-spine, L-spine or W-spine). The user may select the region of interest by clicking the corresponding graphical representation or label. Alternatively, the user may make the selection by typing the anatomical name of the region of interest. Once the user selection is made, the images 404a-b may be automatically created to display the selected region of interest.

Figure 7A:
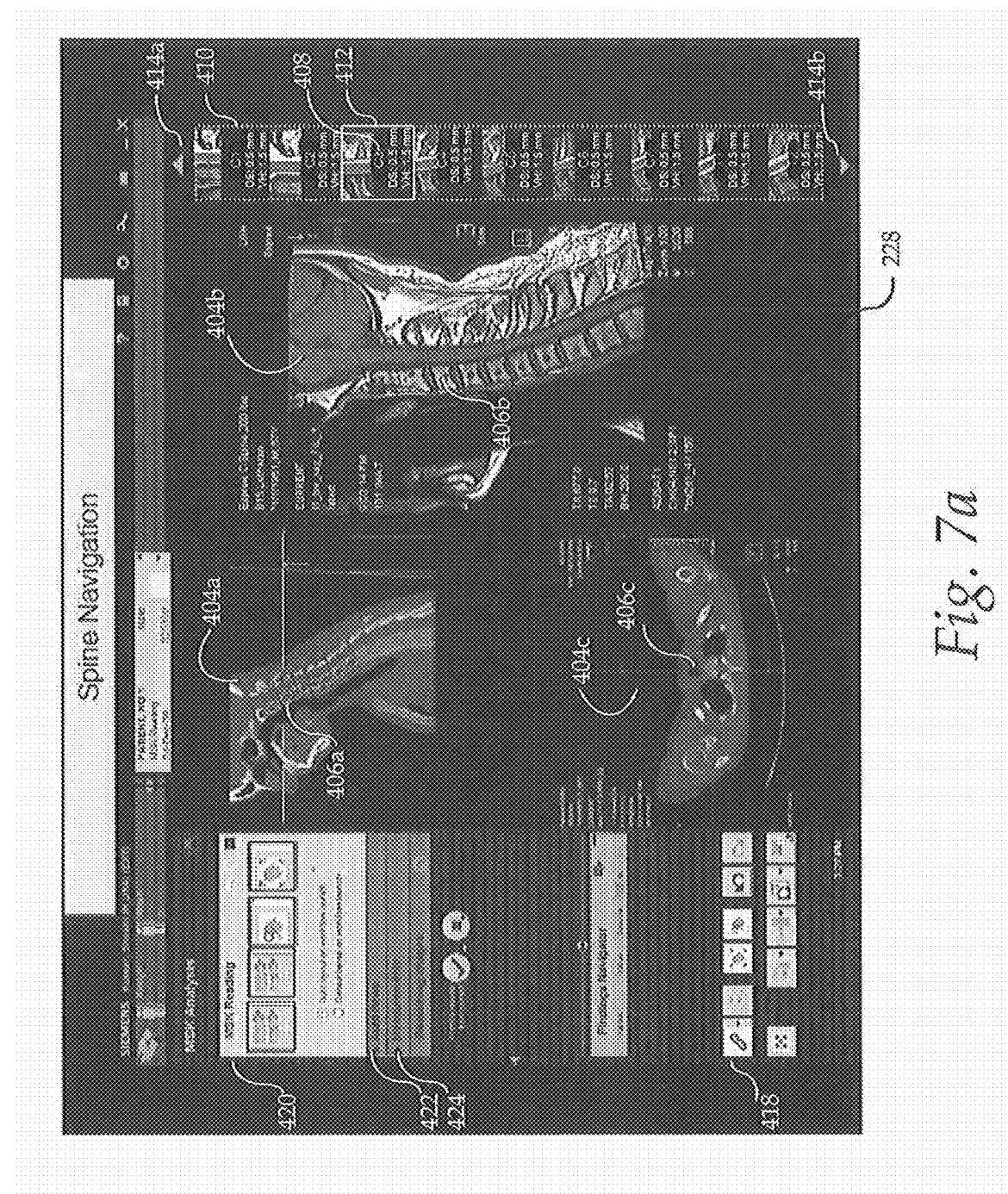
FIG. 7a shows an exemplary graphical user interface with a navigation window.

In another implementation, the first user input is received via a navigation window. FIG. 7a shows an exemplary graphical user interface 228 with an exemplary navigation window 410. The navigation window 410 includes a set of sub-images 412 of the detected vertebrae. Each sub-image 412 may represent a local region of interest, including one or more pre-identified anatomical landmarks. The associated label and other anatomical information (e.g., diameter, height, etc.) may be displayed near, or overlaid on, each sub-image. The navigation window 410 may further include scroll buttons 414a-b for scrolling between available sub-images 412 if there is a greater number of sub-images than the space available in the navigation window. It should be understood that any other type of suitable layouts of the navigation window 410 may also be used. By selecting a sub-image 412 in the navigation window 410, the user may easily navigate to the corresponding region of interest within the medical images 404a-c. Alternatively, the user may be able to directly navigate (or "goto") to the desired region of interest by specifying the anatomical name (e.g., C1) or property (e.g., min/max value, thickness, length, angle, etc.) of the region of interest.

In yet another implementation, the first user input is received when a user selects an anatomical landmark within the region of interest in the medical image directly. Referring to FIG. 7a, for example, when the user selects a particular anatomical landmark 406b in image 404b, the corresponding points (406a and c) in the other images (404a and c) may be highlighted or otherwise visually distinguished. In addition, the corresponding transverse (or axial) view 404c of the selected vertebra (e.g., C3) may also be displayed automatically.

Such accelerated navigation may be achieved by linking (or registering) the medical images 404a-c and sub-images 412 based on the pre-identified anatomical landmarks. "Linking" generally refers to establishing a landmark-by-landmark (or point-by-point) correspondence between multiple images or views (e.g., sagittal, transverse and coronal views). In one implementation, the visualization module 202 links the images by generating a mapping table that maps the coordinates of each anatomical landmark represented in one image to the coordinates of the same anatomical landmark represented in another image. By linking the different images, synchronized scrolling or navigation may be achieved. The user is able to spend less time clicking and scrolling the images to find corresponding points, leaving more time for diagnosis and reporting. Efficiency is further enhanced by avoiding diversion of visual attention across different views, thereby reducing user fatigue and frustration.

Figure 7B:
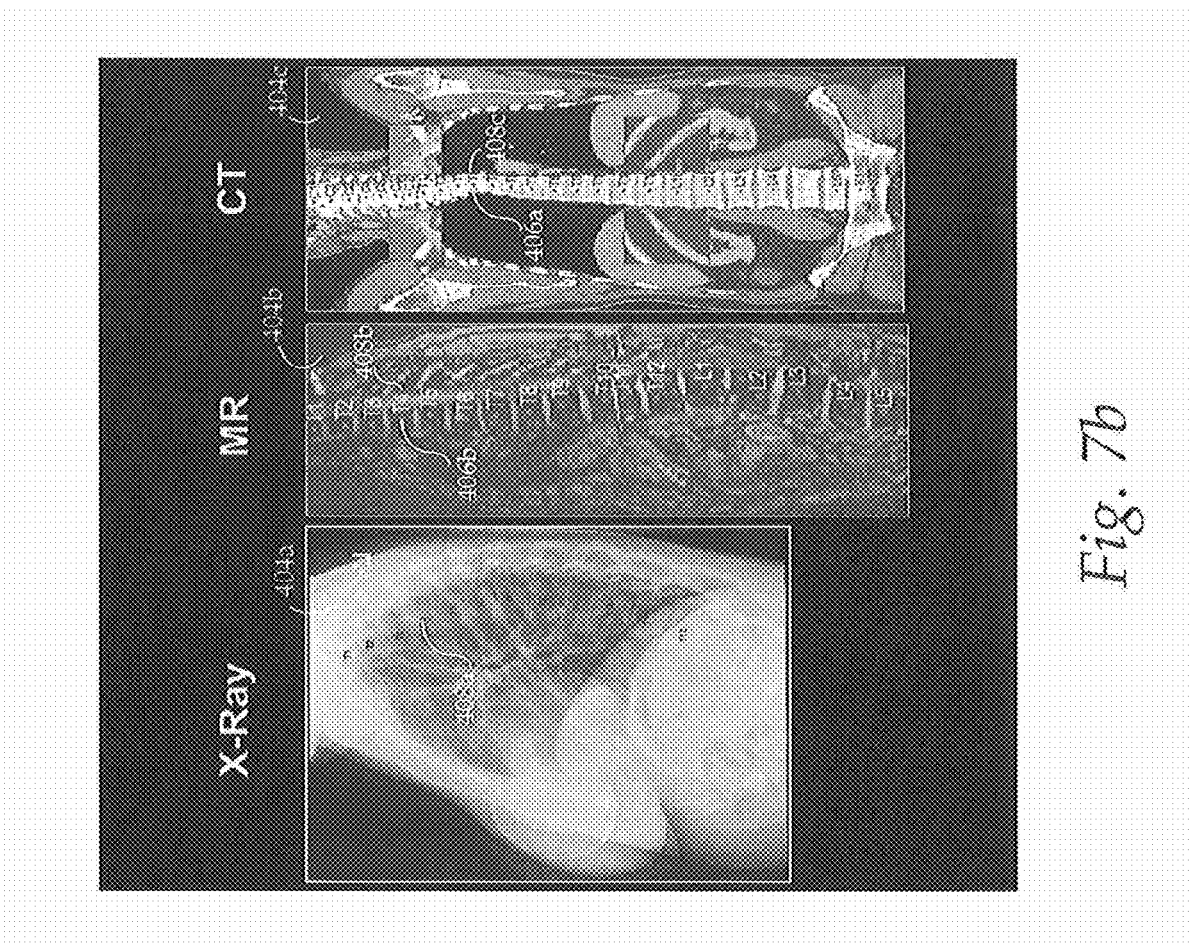
FIG. 7b illustrates the linking of three exemplary images acquired by different modalities.

In one implementation, image linking is performed cross-modally. FIG. 7b illustrates the linking of three exemplary images 404a-c acquired by different modalities. Image 404a is an X-ray image, while images 404b and 404c are MR and CT images respectively. The labels 406a-c of the detected landmarks are linked so as to enable synchronized navigation. For example, when the user clicks on one label in one image, the regions containing the same label in the other images may be highlighted or displayed. It should be understood that other types of images, such as multi-modal images (e.g., CT/MRI, PET/CT, CT/X-Ray, etc.) or images acquired by the same modality with different acquisition protocols, may also be linked. In addition, image linking may also be performed cross-temporally (or cross-sequentially). For example, an MR scout image may be synchronized with the full resolution (or higher quality) images of the entire sequence.

At 306, the user is navigated to the selected region of interest in response to the first user input. The user may be navigated to the selected region of interest by presenting a reformatted view of the region of interest in the main display window, or by highlighting the region of interest within the medical images 404a-c presented in the main display window. If the first user input was received via the "Autoviews" menu 422, the selected region of interest may be presented in reformatted medical images 404a-c based on associated pre-defined view parameters for optimal viewing. Each region of interest in the "Autoviews" menu 422 may be associated with a set of pre-defined view parameters. The view parameters may include geometric parameters (e.g., zoom factor, displacement, rotation angle, viewing direction, orientation of a viewing plane, etc.) and/or color mapping parameters (e.g., transparency, color, contrast, etc.). The view parameters may be statically or dynamically determined to optimally display the selected region of interest.

In one implementation, the selected region of interest is automatically centered in the view presented by the medical image 404a-c. The view orientation may be sagittal, transverse (or axial), or coronal. The view plane or manifold may also be oblique, and its position and orientation may be determined as a function of one or more anatomical landmarks. For example, the view plane or manifold may be constrained to intersect three landmark points, least square fitted to more than three landmark points, and/or offset or re-oriented from those geometrically determined planes. The user may manually change the location and/or orientation of the region of interest by, for example, clicking and dragging a mouse pointer in the image region.

In addition, the selected region of interest may be visually highlighted, or otherwise distinguished, within the medical images 404a-c presented in the main display window. Such visual highlighting may be achieved by, for example, displaying a bounding box delineating the selected region of interest, or changing the color or shading of the indicator marking the anatomical landmarks 406a-c within the selected region of interest.

At 308, a second user input may be received. The second user input indicates the selection of one or more measurement tools for performing automatic evaluations based on the anatomical landmarks. Automatic measurements may include geometric measurements as well as other quantitative information. Geometric measurements useful for MSK analysis include, for instance, spine curvature, vertebral body height, inter-vertebrae distance, disk herniation, spinal canal stenosis, thecal sac diameter, listhesis (slip of vertebra backward/forward), stenosis of foramina (minimum diameter), conus of cord, sacral obliquity, pelvic obliquity, pelvic inclination, scoliosis measurements (e.g., Cobb angles), etc. Other quantitative information, including but not limited to bone-mineral density, relative motion or orthopedic range-of-motion, may also be derived from the anatomical landmarks.

Figure 8:
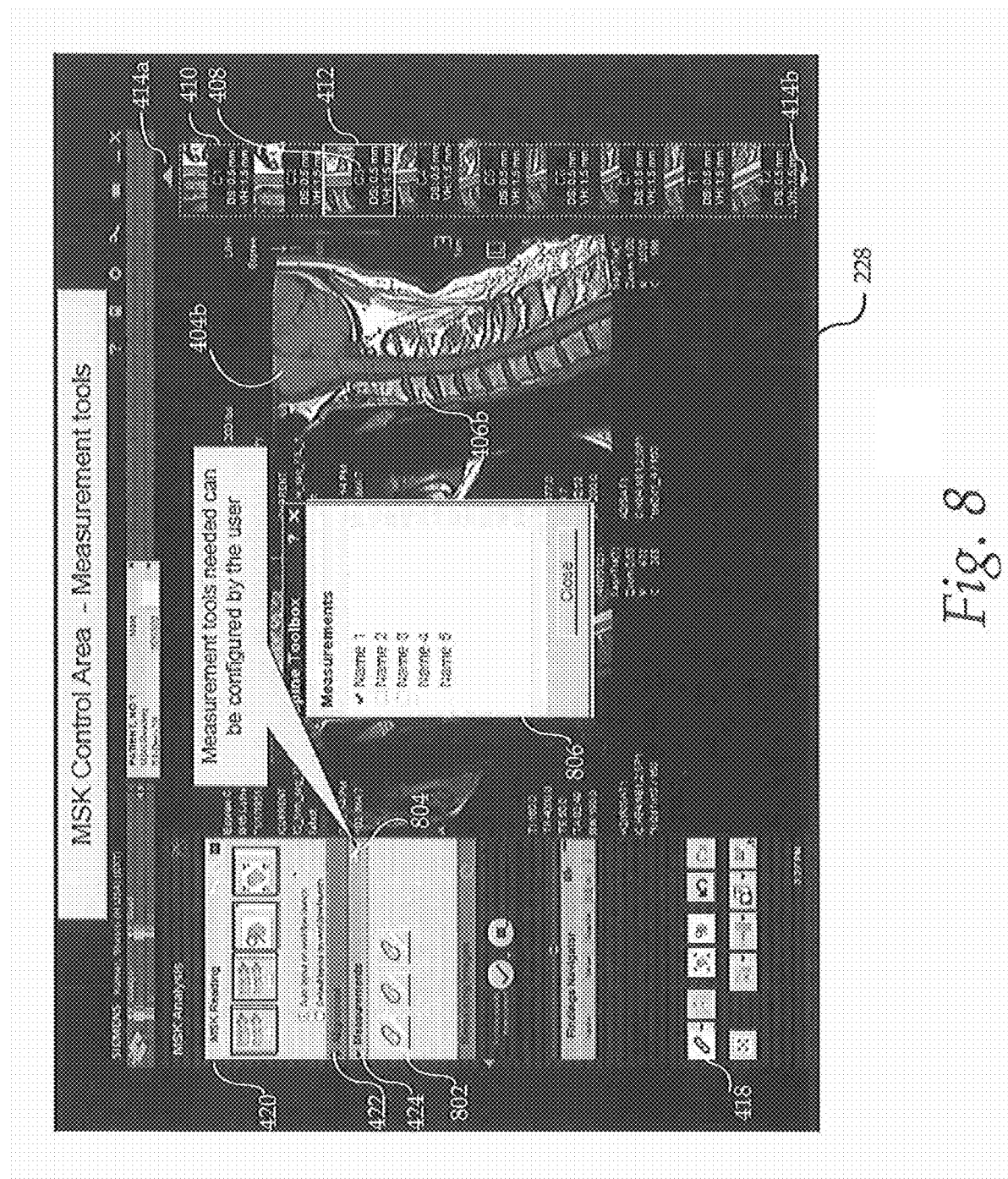
FIG. 8 shows an exemplary graphical user interface with a "Measurements" menu.

The second user input may be received via the "Measurements" menu 424. FIG. 8 shows the exemplary graphical user interface 228 with the "Measurements" menu 424. The "Measurements" menu 424 provides various automatic measurements based on the anatomical landmarks that were previously detected in the images. When the user clicks on one of the graphical icons 802, the automatic measurement is performed using the detected anatomical landmarks. In one implementation, the automatic measurements are configurable by the user. For example, when the user selects the setup graphical icon 804, a pop-up window 806 may be displayed to provide various configuration options. The user may, for instance, configure the name, equation or parameter values of the measurement to be performed. Other configuration options may also be provided.

Figure 9:
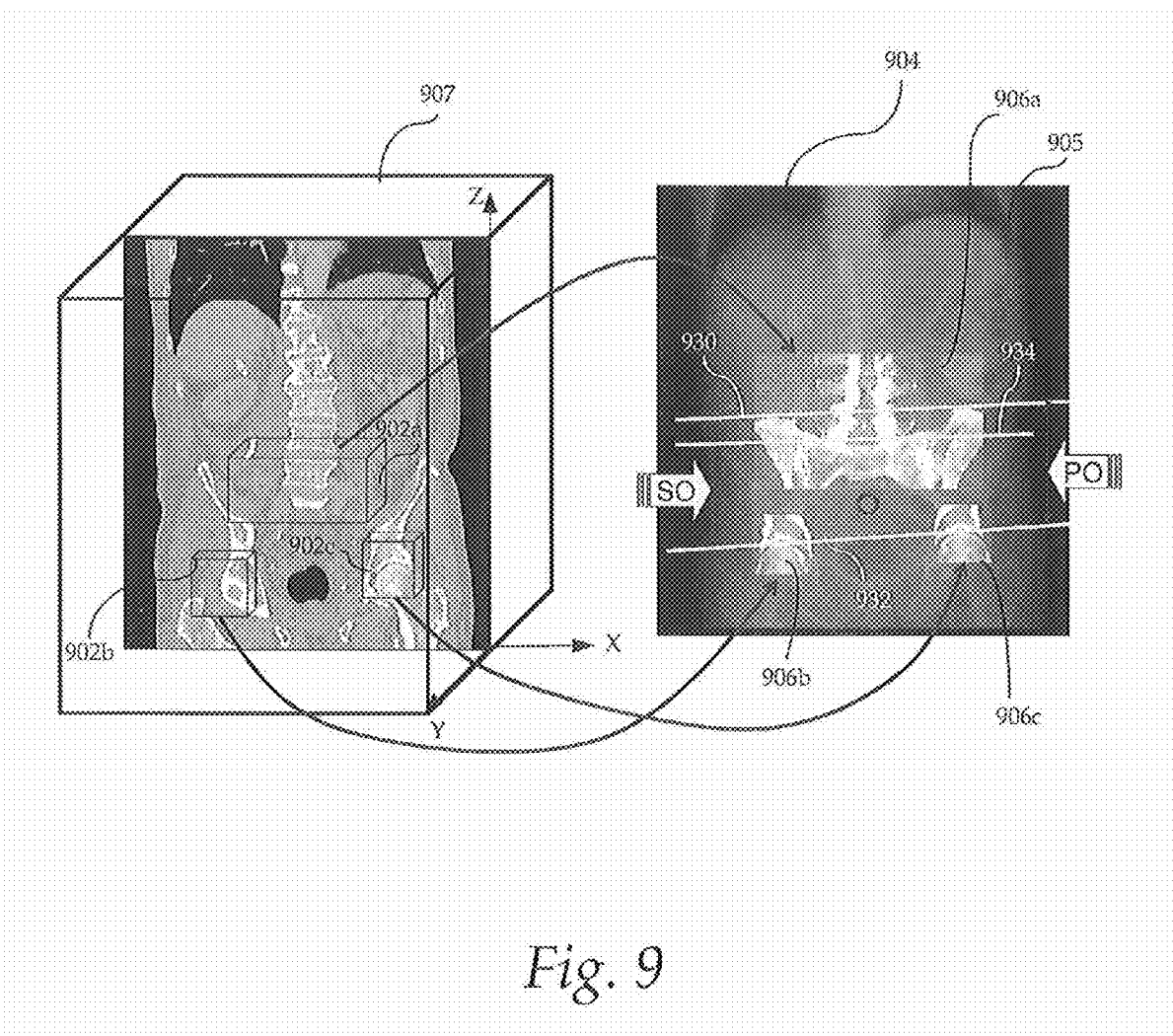
FIG. 9 shows an exemplary measurement that may be performed.

Referring back to FIG. 3, at 310, an evaluation based on the pre-identified landmarks is performed in response to the second user input. In one implementation, the evaluation includes a quantitative measurement. FIG. 9 shows an exemplary quantitative measurement that may be computed. By combining anatomical landmarks 902 detected in different images in one composite image 904, measurements that are not easily or practically obtainable in a single view may now be obtained. For example, cartilage that is visible in one MR sequence image and bony structural landmarks or structures that are visible in another sequence may be combined to derive a measurement (e.g., cartilage thickness). The composite image 904 may be reconstructed using the techniques described in, for example, U.S. patent application Ser. No. 13/111,376 filed May 19, 2011, which is herein incorporated by reference in its entirety.

In one implementation, the composite image 904 comprises a background image 905 and one or more foreground images 906a-c. The background image 905 serves to provide the contextual information or global overview of the structure of interest, while the foreground images 906a-c serve to enhance the visualization of a local ROI (or anatomical landmarks). The background image may be a multi-planar reconstruction (MPR) image, a curved MPR image, a summation-based, an average-based or a filtering-based projection image, while the local images may be maximum or minimum intensity projection images. In one implementation, the background image 905 is reconstructed by, for example, integrating the 3D image volume 907 in a front-to-back direction or re-sampling the image data in the neighborhood about each sampling point on a flat or curve plane. The foreground images 906a-c may be reconstructed by, for example, performing a maximum (or minimum) intensity projection (MIP) technique. Other types of visual enhancement techniques, such as volume rendering technique (VRT), thick MPR, or average projection, may also be employed in either a local or global neighborhood.

Anatomical landmarks may be detected prior to or after the composite image 904 is reconstructed. Measurements may then be automatically or semi-automatically performed using these anatomical landmarks. For example, the sacral obliquity (SO) or tilt may be computed by determining the sacral line 934 and femoral line 932. Similarly, the pelvic obliquity (PO) may be computed based on the pelvic line 930 and femoral line 932 defined by anatomical landmarks detected in the same composite image 904. By presenting the anatomical landmarks (or measurement points) in the same composite image 904, the need to scroll through many images in search of such points in different planes is conveniently eliminated, thereby saving much time, user frustration and error.

Other types of quantitative information may also be derived based on the anatomical landmarks. In another implementation, bone-mineral density measurement is performed. Bone-mineral density may be obtained by measuring the mass to volume ratio of a bone structure. To obtain the volume of the bone structure, one or more measurements are obtained across multiple vertebral bodies. The one or more measurements are provided as input to a predictive model that is proxy to, and predictive of, measurements that would be obtained using bone-mineral density measurements obtained with other proven techniques.

In addition, relative motion may be identified, and compensated for, by identifying common landmarks and structures in both images. Orthopedic range-of-motion may be computed from radiological, visible light or range images. Range-of-motion generally refers to the distance and direction a joint can move to its full potential. Each specific joint has a normal range of motion that is expressed in degrees.

The measurements may be used to provide decision support in the diagnosis and/or treatment of abnormalities (or diseases). In the case of MSK analysis, for instance, the Cobb angle may be used to diagnose scoliosis, which is the abnormal curving of the spine that can be corrected using devices that place the spine or help the spine be in the most ideal mechanical situation.

Figure 10:
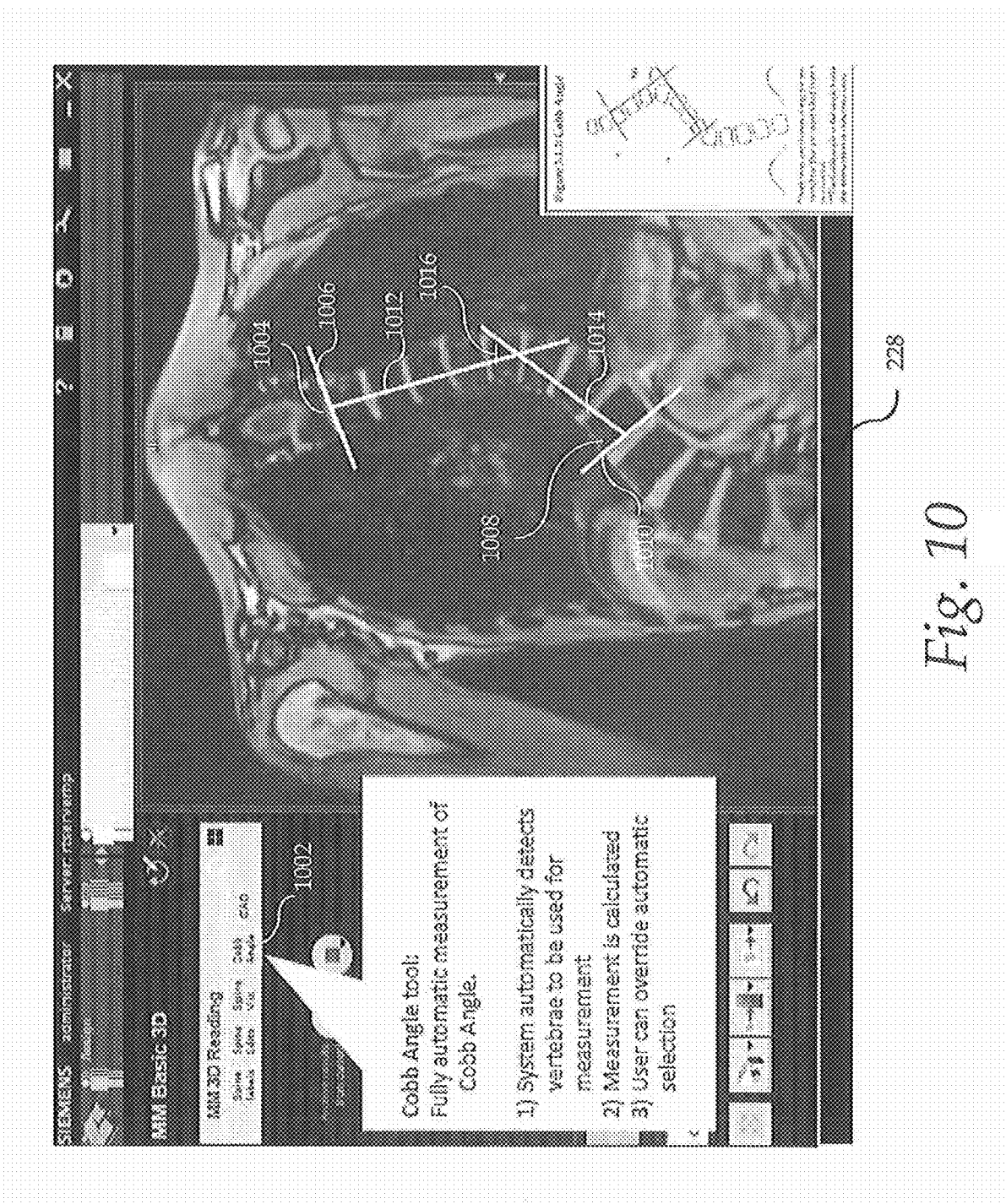
FIG. 10 shows an exemplary graphical user interface with a Cobb angle measurement tool.

FIG. 10 shows an exemplary graphical user interface 228 with a Cobb angle measurement tool 1002. The measurement of the Cobb angle may be fully automatic or semi-automatic. In one implementation, the evaluation module 206 automatically measures the Cobb angle by detecting the most tilted vertebra 1004 at the top of the curved segment and the most tilted vertebra 1008 at the bottom of the curved segment. The user may confirm or override the locations of the detected vertebrae. Next, a parallel line 1006 to the superior vertebral end plate and a parallel line 1010 to the inferior vertebral end plate are automatically determined. Intersecting perpendicular lines (1012, 1014) may then be determined from the two parallel lines (1006, 1010) to compute the Cobb angle 1016.

Other types of evaluation may also be provided to support decision making. For example, developmental abnormalities (or diseases) of the ribs, vertebrae or spinal cord may be detected by the existence of 6th lumbar vertebra or 13th thoracic vertebra, absence of 12th thoracic vertebra or 5th lumbar vertebra, sacralization or lumberalization, etc. Dark bone border intensity information from an MRI image may be used to detect bone metastasis, fractures, osteoporosis, Schmorl's nodes, osteochondrosis, edemas, inflammation, cysts, hemangiomas, arthrosis and/or bone infarct. See, for example, U.S. Pat. No. 7,920,730, the disclosure of which is herein incorporated by reference.

Figure 11:
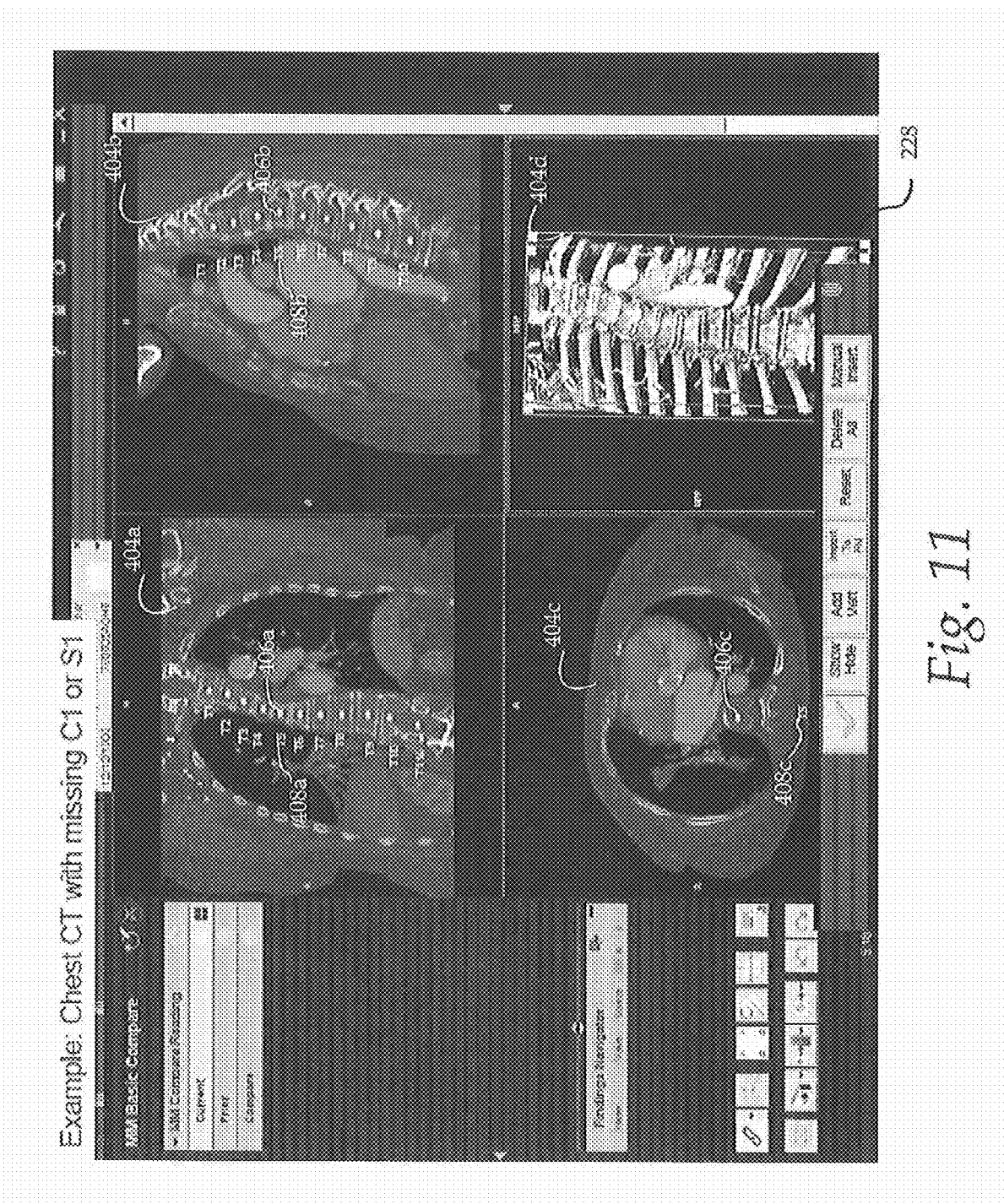
FIG. 11 shows an exemplary graphical user interface for detecting a missing vertebra.

FIG. 11 shows an exemplary graphical user interface 228 for detecting a missing vertebra. As shown, a coronal view 404a, a sagittal view 404b, a transverse view 404c and a volume-rendered view 404d view of a chest CT image is shown. The views 404a-d may be linked in accordance with the techniques previously described so as to enable synchronized scrolling and accelerated navigation. As the user navigates the images, it may be discovered that, for example, the topmost cervical vertebra (or atlas) C1 or the first sacral vertebra 51 is missing. Alternatively, the evaluation module 206 may automatically detect the missing vertebra and notify the user via the user interface 228.

Referring back to FIG. 3, at 312, the process 300 determines if all key observations are made. This may be achieved by looking up a pre-defined checklist of observations to be made. If any key observation on the checklist has not been made, the graphical user interface 228 may prompt the user via, for example, a pop-up dialogue box, about the remaining observations. If the user desires to continue analyzing the images, the process 300 continues at 304. If all key observations have been made or the user elects to skip the remaining key observations on the checklist, the process 300 proceeds to step 314.

In one implementation, the checklist is derived from a standardized reporting template (or report template). The reporting template may include a plurality of documentation areas designed to present clinical evidence in accordance with best practices in radiology reporting. One example of such a reporting template is the RSNA Radiology Report Template. In the case of CT or MR spine studies, for instance, the reporting template may include documentation areas for general observations (e.g., lordosis/kyphosis, alignment, spinal canal, anatomy, etc.), vertebral observations applicable to cervical (C2-C7), thoracic (T1-T12) and lumbar (L1 to S1) sections, and interspace observations applicable to cervical (C2/3 to C7/T1), thoracic (T1/2 to T11/12), lumbar (L1/2 to L5/S1) sections. The checklist of key observations to be made by the system 100 and/or the user may be extracted from such standardized reporting template so as to ensure that best practices are followed.

If all the key observations have been made, the process 300 continues to 314. At 314, a clinical report based on the evaluation is output. The layout of the clinical report may be defined in accordance with reporting template, as previously described. In one implementation, the clinical report summarizes the clinical evidence (e.g., key observations, measurements, etc.), diagnostic conclusions and/or recommendations made by the system 100 and the user. The clinical report may be presented via the graphical user interface 228 so that the treating doctor can determine the diagnosis and be informed about any abnormalities when appropriate. The report may then be used as a basis for planning an operation, arranging radiotherapy or treatment regime.

It should be noted that the graphical user interface 228 may further include additional toolbars, including but not limited to, a general menu 418 and "MSK reading" menu 420. The general menu 418 may provide buttons for performing common functions, such as image view functions (e.g., zoom, pan, etc.), image edit functions (e.g., undo, insert, rotate, cut, paste, capture, etc.), file functions (e.g., print, open, save, etc.), and so forth. The "MSK reading" menu 420 allows the user to insert, delete or rename labels, show or hide image markers and/or lines, and show or hide image text. It should be understood that other menu options and toolbars may also be provided.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

Further, although method or process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

The invention claimed is:

1. A method for supporting a diagnostic workflow from a computer system, comprising:
   (a) linking, based on a set of pre-identified anatomical landmarks of one or more structures of interest, multiple medical images to establish a landmark-by-landmark correspondence by mapping coordinates of one of the anatomical landmarks represented in one of the medical images to the coordinates of the same anatomical landmark represented in another of the medical images, wherein the anatomical landmarks are pre-identified to have anatomical significance;
   (b) presenting, via a display device, the pre-identified anatomical landmarks and automatically-generated text labels of corresponding names within one or more of the medical images;
   (c) receiving, via an input device, a first user input selecting at least one of one or more regions of interest, wherein the region of interest includes one or more of the anatomical landmarks;
   (d) navigating to, via the display device, the selected region of interest in response to the first user input; and
   (e) editing the automatically-generated text labels in response to user selections from a hierarchical menu of labels associated with different levels of abstraction of the one or more structures of interest.

2. The method of claim 1 wherein the one or more structures of interest comprise one or more musculoskeletal structures.

3. The method of claim 1 wherein the pre-identified anatomical landmarks are associated with the one or more structures of interest within multiple medical images acquired by different modalities.

4. The method of claim 1 wherein the pre-identified anatomical landmarks are associated with the one or more structures of interest within multiple medical images acquired across different times.

5. The method of claim 1 wherein the pre-identified anatomical landmarks are associated with the one or more structures of interest within multiple medical images acquired by a single modality using different acquisition protocols.

6. The method of claim 1 further comprising creating one or more optimal views of the one or more medical images including the set of pre-identified anatomical landmarks.

7. The method of claim 6 wherein the one or more optimal views are created by performing maximum or minimum intensity projection, multi-planar reconstruction (MPR), curved MPR, curved planar reformatting, summation-based projection, average-based projection or filtering-based projection on the one or more medical images.

8. The method of claim 6 wherein the one or more optimal views are created by normalizing, scaling or coding the one or more medical images.

9. The method of claim 6 wherein the one or more optimal views are created by determining an orientation or position of a view plane or manifold as a function of at least one of the anatomical landmarks.

10. The method of claim 1 further comprising automatically detecting the anatomical landmarks by performing thresholding, region-growing, segmentation, edge detection algorithms, machine learning, or a combination thereof.

11. The method of claim 1 further comprising automatically updating other text labels in response to a change made to any one of the text labels.

12. The method of claim 1 wherein the text labels of the pre-identified anatomical landmarks within one or more scout images are automatically generated and propagated to images that share a common frame of reference with the one or more scout images.

13. The method of claim 1 wherein the one or more regions of interest are associated with pre-defined view parameters.

14. The method of claim 1 further comprising displaying sub-images of the one or more regions of interest in a navigation window.

15. The method of claim 14 wherein the first user input comprises a user selection of at least one of the sub-images.

16. The method of claim 1 wherein the first user input comprises an anatomical name of the at least one of the one or more regions of interest.

17. The method of claim 1 wherein the first user input comprises a user selection of an anatomical landmark within the at least one of the one or more regions of interest.

18. The method of claim 1 wherein the anatomical landmarks represent extremities, mid-points or local regions of the one or more structures of interest that are of anatomical relevance.

19. The method of claim 1 wherein the medical images represent different views of the one or more structures of interest.

20. The method of claim 1 wherein the multiple medical images are acquired by using different modalities, using different acquisition protocols or at different time points.

21. The method of claim 1 wherein navigating to the selected region of interest comprises displaying a reformatted view of the selected region of interest.

22. The method of claim 1 wherein navigating to the selected region of interest comprises visually highlighting the selected region of interest.

23. The method of claim 1 further comprising:
receiving a second user input selecting one or more measurement tools; and
automatically determining an evaluation based on one or more of the set of anatomical landmarks in response to the second user input.

24. The method of claim 23 wherein the evaluation comprises a quantitative measurement of spine curvature, vertebral body height, inter-vertebrae distance, disk herniation, spinal canal stenosis, thecal sac diameter, listhesis, stenosis of foramina, conus of cord, sacral obliquity, pelvic obliquity, pelvic inclination, Cobb angle, bone-mineral density, relative motion or range-of-motion.

25. The method of claim 23 further comprising enabling a user to configure, via a graphical user interface, the one or more measurement tools.

26. The method of claim 23 further comprising combining multiple landmarks selected from the set of pre-identified anatomical landmarks in one composite image and determining the evaluation based on the multiple landmarks.

27. The method of claim 23 wherein automatically determining an evaluation comprises detecting a missing vertebra.

28. The method of claim 23 further comprising generating a clinical report based on the evaluation.

29. The method of claim 1 further comprising repeating one or more of steps (a), (b) and (c) if a checklist indicates that there is at least one remaining key observation to be made.

30. A non-transitory computer readable medium embodying a program of instructions executable by machine to perform steps for supporting a diagnostic workflow, the steps comprising:
(a) linking, based on a set of pre-identified anatomical landmarks of one or more structures of interest, multiple medical images to establish a landmark-by-landmark correspondence by mapping coordinates of one of the anatomical landmarks represented in one of the medical images to the coordinates of the same anatomical landmark represented in another of the medical images, wherein the anatomical landmarks are pre-identified to have anatomical significance;
(b) presenting the pre-identified anatomical landmarks associated with one or more structures of interest and automatically-generated text labels of corresponding names within one or more of the medical images;
(c) receiving a first user input selecting at least one of one or more regions of interest, wherein the region of interest includes one or more of the anatomical landmarks;
(d) navigating to the selected region of interest in response to the first user input; and
(e) editing the automatically-generated text labels in response to user selections from a hierarchical menu of labels associated with different levels of abstraction of the one or more structures of interest.

31. A system for supporting a diagnostic workflow, comprising:
a non-transitory memory device for storing computer readable program code;
a processor in communication with the memory device, the processor being operative with the computer readable program code to:
(a) link, based on a set of pre-identified anatomical landmarks of one or more structures of interest, multiple medical images to establish a landmark-by-landmark correspondence by mapping coordinates of one of the anatomical landmarks represented in one of the medical images to the coordinates of the same anatomical landmark represented in another of the medical images, wherein the anatomical landmarks are pre-identified to have anatomical significance;
(b) present the pre-identified anatomical landmarks associated with one or more structures of interest and automatically-generated text labels of corresponding names within one or more of the medical images;
(c) receive a first user input selecting at least one of one or more regions of interest, wherein the region of interest includes one or more of the anatomical landmarks;

(d) navigate to the selected region of interest in response to the first user input; and
(e) edit the automatically-generated text labels in response to user selections from a hierarchical menu of labels associated with different levels of abstraction of the one or more structures of interest.

* * * * *